(12) United States Patent
Villafane

(10) Patent No.: US 11,427,996 B2
(45) Date of Patent: Aug. 30, 2022

(54) AIR FRESHENER DISPENSER ASSEMBLY

(71) Applicant: William Villafane, Avondale, PA (US)

(72) Inventor: William Villafane, Avondale, PA (US)

(*) Notice: Subject to any disclaimer, the term of this patent is extended or adjusted under 35 U.S.C. 154(b) by 75 days.

(21) Appl. No.: 16/862,974

(22) Filed: Apr. 30, 2020

(65) Prior Publication Data

US 2021/0340748 A1 Nov. 4, 2021

(51) Int. Cl.
*E03D 9/00* (2006.01)
*A61L 9/14* (2006.01)

(52) U.S. Cl.
CPC ............... *E03D 9/007* (2013.01); *A61L 9/14* (2013.01); *A61L 2209/111* (2013.01); *A61L 2209/15* (2013.01)

(58) Field of Classification Search
None
See application file for complete search history.

(56) References Cited

U.S. PATENT DOCUMENTS

| | | |
|---|---|---|
| 3,336,603 A | 8/1967 | Leland |
| 4,670,916 A | 6/1987 | Bloom |
| 6,029,286 A * | 2/2000 | Funk ................. E03D 9/005 4/223 |
| 6,625,821 B2 | 9/2003 | Lhoste |
| 6,654,971 B1 | 12/2003 | Middleton |
| 7,676,856 B1 | 3/2010 | Graham, III |
| 8,631,519 B1 | 1/2014 | Belliard |
| 9,332,885 B1 | 5/2016 | Todd |
| 2004/0128751 A1 | 7/2004 | Haq |
| 2008/0028505 A1 * | 2/2008 | Penn .................. E03D 9/007 4/231 |
| 2010/0205731 A1 * | 8/2010 | Muhlhausen ....... B05B 9/0811 4/223 |
| 2016/0024773 A1 | 6/2016 | Page |

FOREIGN PATENT DOCUMENTS

WO  WO2009086948  7/2009

* cited by examiner

*Primary Examiner* — Jelitza M Perez

(57) ABSTRACT

An air freshener dispenser assembly includes a dispensing unit for containing a chemical fragrance. The dispensing unit releases a measured amount of the chemical fragrance when the dispensing unit is turned on. In this way the dispensing unit can enhance odors associated with an area proximate the dispensing unit. A pair of switches is each of the switches is coupled the dispensing unit and each of the switches is turned on when a user sits on the seat. The dispensing unit is turned on when the switches are turned on. In this way the dispensing unit reduces odors associated with the user employing the toilet.

6 Claims, 7 Drawing Sheets

AIR FRESHENER DISPENSER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to dispenser devices and more particularly pertains to a new dispenser device for reducing unpleasant odors associated with a toilet.

(2) Description of Related Art Including Information Disclosed Under 37 CFR 1.97 and 1.98

The prior art relates to dispenser devices including an aerosol canister that is mountable to a toilet seat thereby facilitating an aerosol fragrance to be released into a toilet. The prior art discloses a mount that supports a pair of canisters on a toilet bowl for spraying an aerosol fragrance. The prior art discloses a variety of air fresheners that can be suspended on a toilet bowl and which include a cartridge of fragrance that is diffusely released from the air fresheners. Additionally, the prior art discloses a variety of dispensers that include an aerosol canister and a spraying mechanism that is in communication with a seat of the toilet for spraying an aerosol when a person sits on the seat of the toilet.

BRIEF SUMMARY OF THE INVENTION

An embodiment of the disclosure meets the needs presented above by generally comprising a dispensing unit for containing a chemical fragrance. The dispensing unit releases a measured amount of the chemical fragrance when the dispensing unit is turned on. In this way the dispensing unit can enhance odors associated with an area proximate the dispensing unit. A pair of switches is each of the switches is coupled the dispensing unit and each of the switches is turned on when a user sits on the seat. The dispensing unit is turned on when the switches are turned on. In this way the dispensing unit reduces odors associated with the user employing the toilet.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
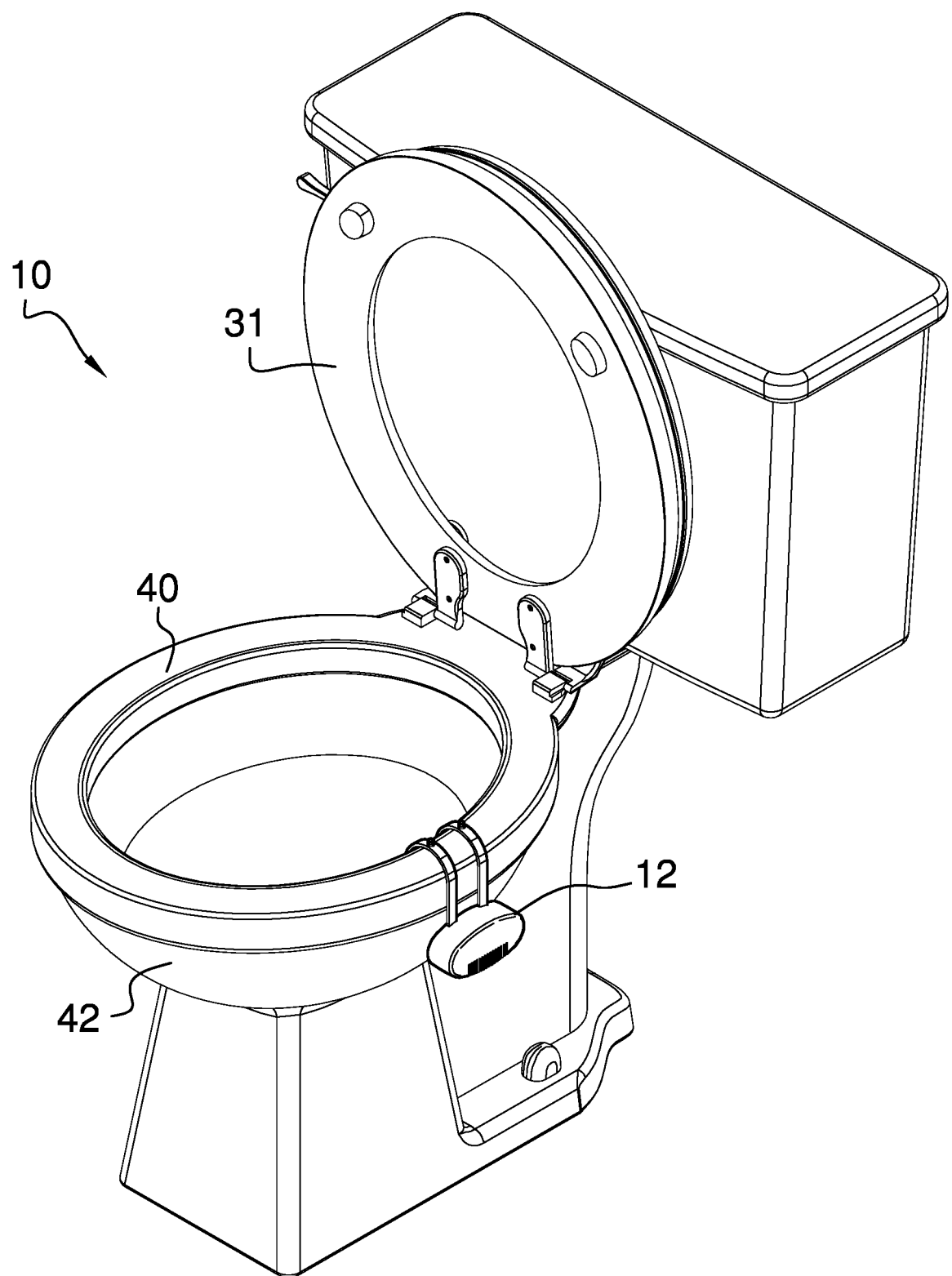
FIG. 1 is a perspective in-use view of an air freshener dispenser assembly according to an embodiment of the disclosure.
Figure 2:
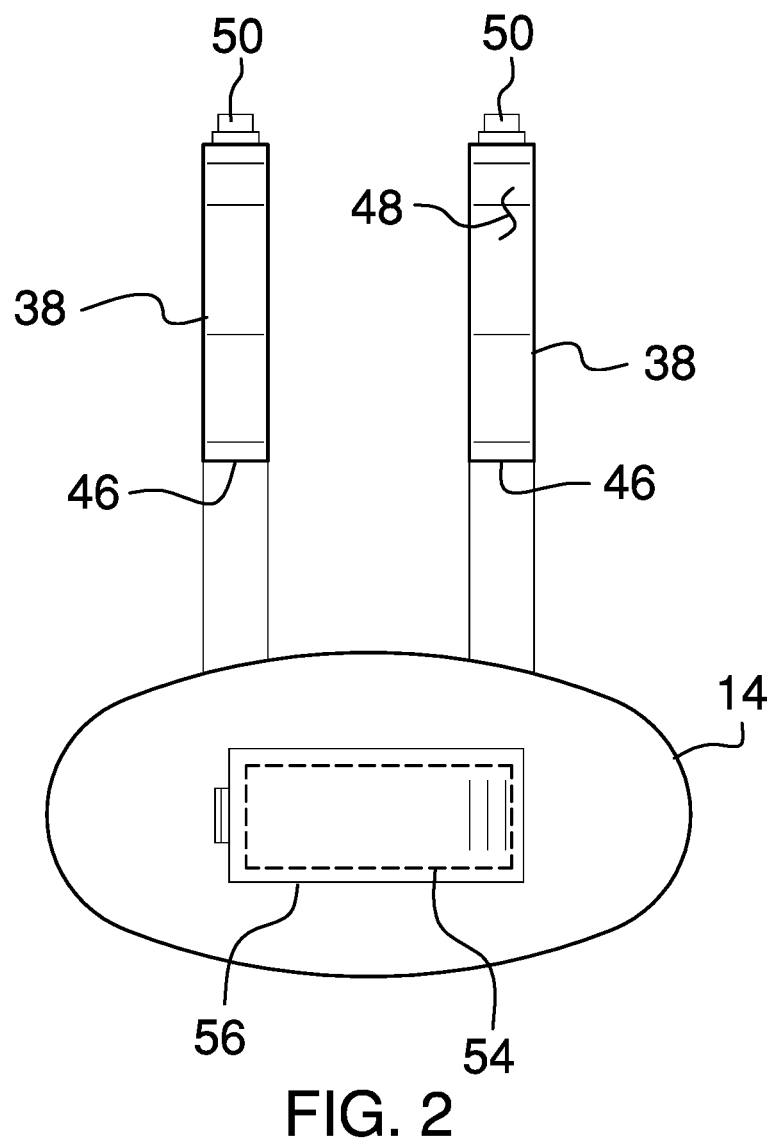
FIG. 2 is a back view of an embodiment of the disclosure.
Figure 3:
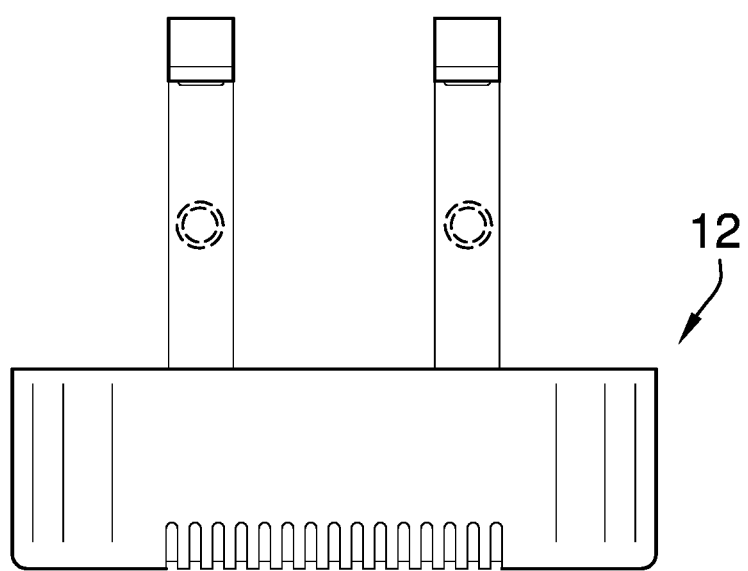
FIG. 3 is a bottom phantom view of an embodiment of the disclosure.
Figure 4:
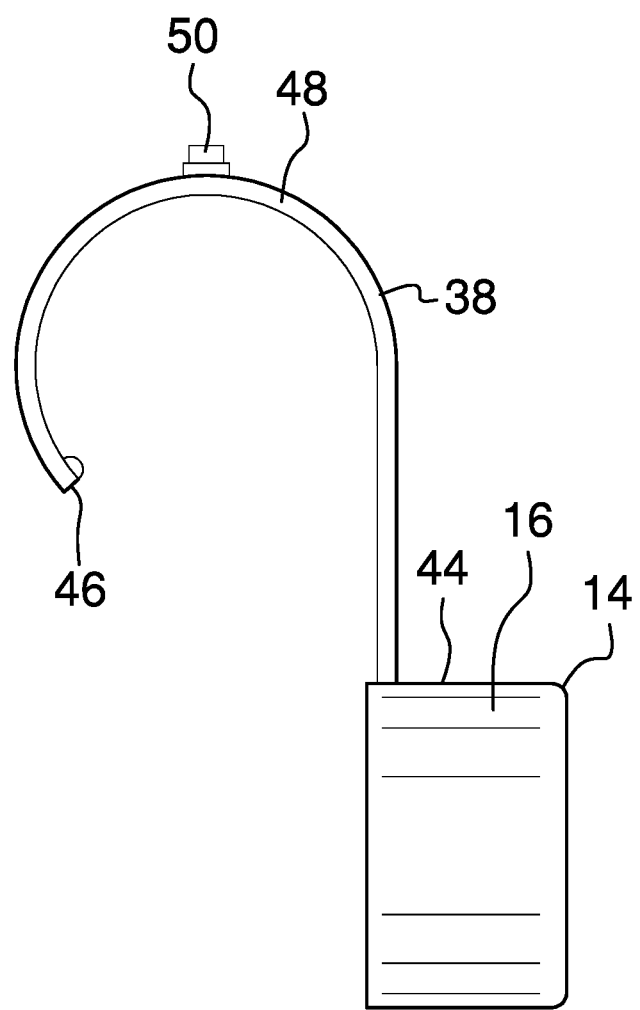
FIG. 4 is a right side view of an embodiment of the disclosure.
Figure 5:
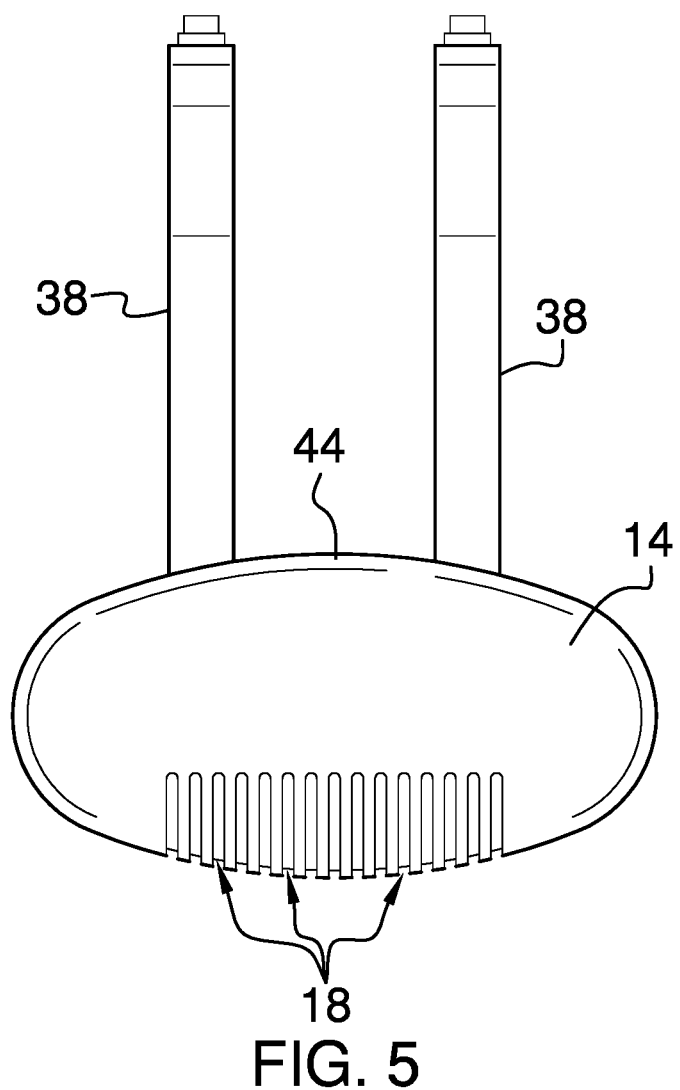
FIG. 5 is a front view of an embodiment of the disclosure.
Figure 6:
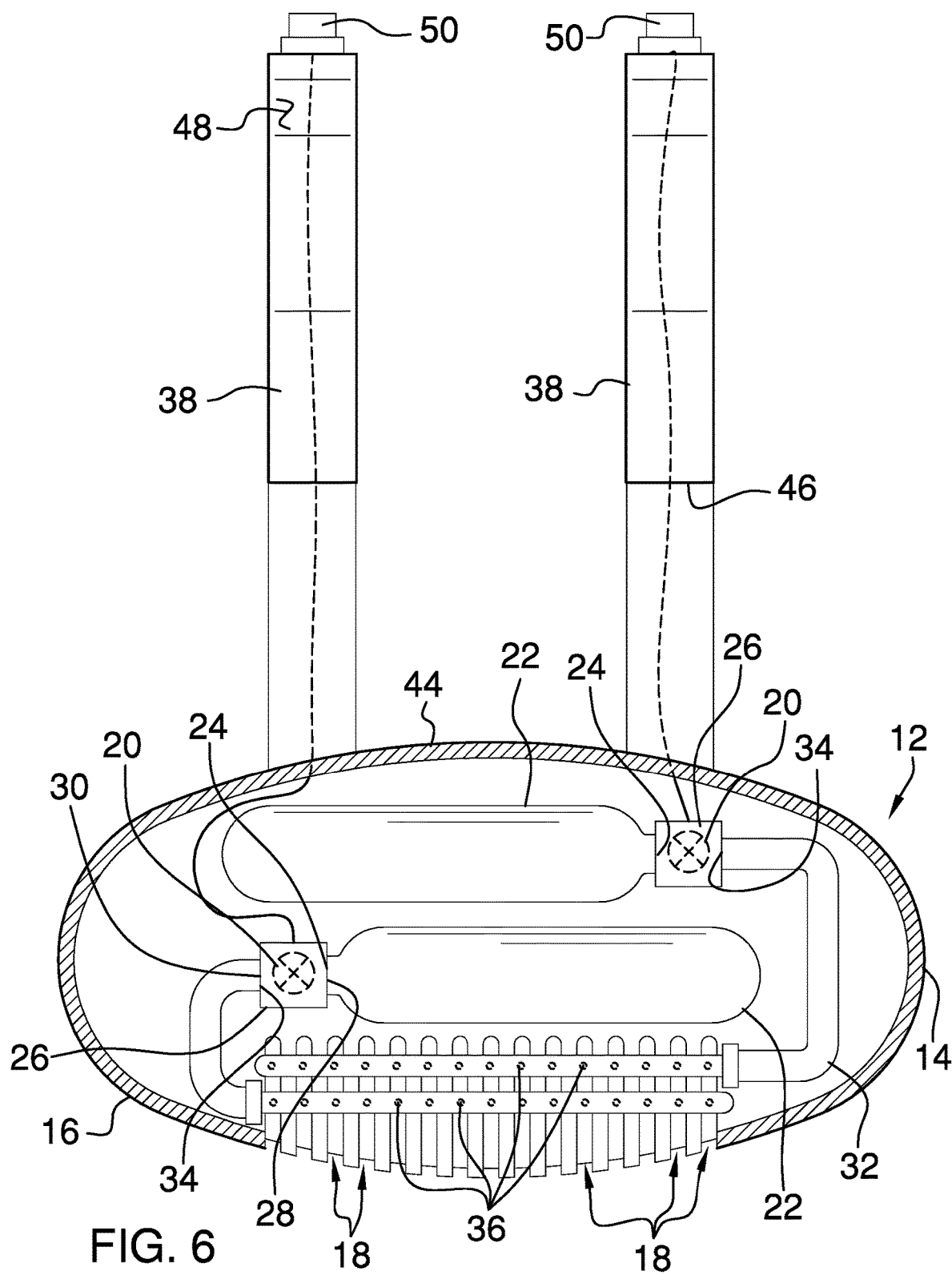
FIG. 6 is a front cutaway view of an embodiment of the disclosure.
Figure 7:
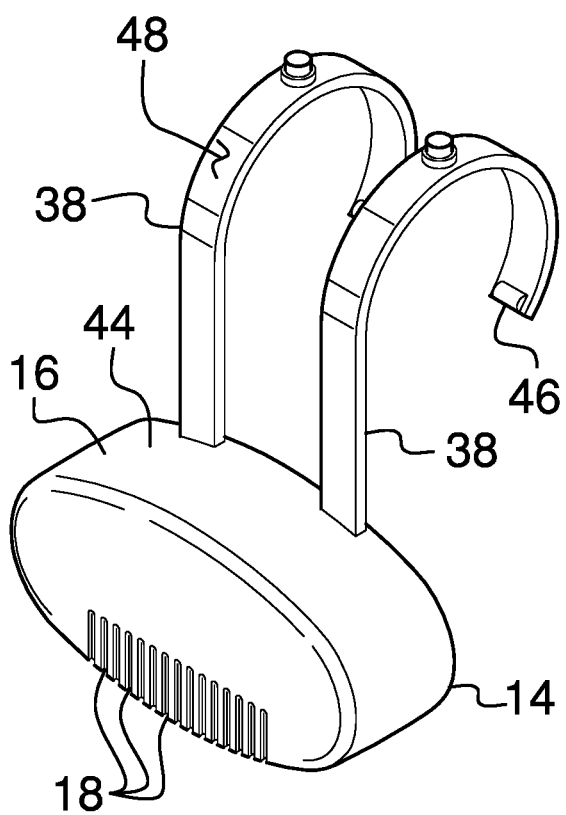
FIG. 7 is a perspective view of an embodiment of the disclosure.

With reference now to the drawings, and in particular to FIGS. 1 through 7 thereof, a new dispenser device embodying the principles and concepts of an embodiment of the disclosure and generally designated by the reference numeral 10 will be described.

As best illustrated in FIGS. 1 through 7, the air freshener dispenser assembly 10 generally comprises a dispensing unit 12 that contains a chemical fragrance. The dispensing unit 12 releases a measured amount of the chemical fragrance when the dispensing unit 12 is turned on. In this way the dispensing unit 12 enhances odors associated with an area proximate the dispensing unit 12. The dispensing unit 12 comprises a housing 14 that has an outer wall 16. The outer wall 16 has a plurality of vents 18 each extending into an interior of the housing 14 to pass air therethrough.

The dispensing unit 12 includes a control circuit 20 that is positioned in the housing 14. The control circuit 20 receives a first input and the control circuit 20 receives a second input. The dispensing unit 12 includes a pair of reservoirs 22 that is each positioned within the housing 14. Each of the reservoirs 22 has an outlet 24 and each of the reservoirs 22 contains an aerosol fragrance.

The dispensing unit 12 includes a pair of valves 26 that each has an input 28 and an output 30. Each of the valves 26 is actuatable into a closed condition to inhibit fluid communication between the input 28 and the output 30. Conversely, each of the valves 26 is actuatable into an open condition to facilitate fluid communication between the input 28 and the output 30. The input 28 of each of the valves 26 is fluidly coupled to the outlet 24 of a respective one of the reservoirs 22. Each of the valves 26 is electrically coupled to the control circuit 20 and each of the valves 26 is normally actuated into the closed condition to retain the aerosol fragrance in the respective reservoir. Additionally, each of the valves 26 may comprise an electrically controlled air valve or the like.

Each of the valves 26 is actuated into the open condition for a pre-determined duration of time when the control circuit 20 receives the first input to release a metered amount of the aerosol fragrance. Moreover, each of the valves 26 is actuated into the open condition two times each time the control circuit 20 receives the first input. Each of the valves 26 is actuated into the open condition for a pre-determined duration of time when the control circuit 20 receives the second input to release a metered amount of the aerosol fragrance. In this way a metered amount of aerosol fragrance is sprayed two times when the user sits on a seat 31 of the toilet and a metered amount of aerosol fragrance is sprayed one time when the user stands up from the seat 31.

The dispensing unit 12 includes a manifold 32 that is positioned within the housing 14. The manifold 32 has a pair of intakes 34 and a plurality of exhausts 36, and each of the intakes 34 is fluidly coupled to the output 30 of a respective one of the valves 26. In this way the manifold 32 receives the aerosol fragrance. Each of the exhausts 36 is aligned with a respective one of the vents 18 in the outer wall 16 of the housing 14 to release the aerosol fragrance through the vents 18.

A pair of arms 38 is provided and each of the arms 38 is coupled to and extends away from the dispensing unit 12. Each of the arms 38 is curved thereby facilitating each of the arms 38 to rest on a rim 40 of a toilet bowl 42. In this way the dispensing unit 12 can be suspended from the toilet bowl 42. Each of the arms 38 extends upwardly from a top side 44 of the outer wall 16 of the housing 14. Each of the arms 38 has a distal end 46 with respect to the housing 14 and a top surface 48, and each of the arms 38 curves downwardly between the top side 44 of the outer wall 16 and the distal end 46.

The dispensing unit 12 includes a pair of switches 50 that is each coupled to a respective one of the arms 38. Each of the switches 50 is positioned beneath the seat 31 of the toilet thereby facilitating each of the switches 50 to be turned on when a user sits on the seat 31. Each of the switches 50 is turned off when the user is not sitting on the seat 31. Additionally, each of the switches 50 is in electrical communication with the dispensing unit 12. The dispensing unit 12 is turned on when the switches 50 are turned on to reduce odors associated with the user employing the toilet.

Each of the switches 50 is positioned on the top surface 48 of the respective arm 38 and each of the switches 50 is aligned with an apex of the curvature of the respective arm 38. In this way each of the switches 50 are positioned such that the seat 31 pressed downwardly on the switches 50 when the user sits on the seat 31. Each of the switches 50 is electrically coupled to the control circuit 20 and the control circuit 20 receives the first input when the switches 50 are turned on. Additionally, the control circuit 20 receives the second input when the switches 50 are turned off after is turned on. A power supply 54 is positioned in the housing 14, the power supply 54 is electrically coupled to the control circuit 20 and the power supply 54 comprises at least one battery. A battery cover 56 is removably coupled to the outer wall 16 of the housing 14 and the power supply 54 is positioned behind the battery cover 56.

In use, the arms 38 are placed over the rim 40 of the toilet bowl 42 thereby facilitating the seat 31 of the toilet to engage the switches 50 when the user sits on the toilet seat 31. Thus, the dispensing unit 12 releases two metered sprays of the aerosol fragrance to reduce odors associated with the toilet. The dispensing unit 12 releases an additional metered spray of the aerosol fragrance when the user stands up from the seat 31. Additionally, the dispensing unit 12 is replaced with the reservoirs 22 become depleted.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. An air freshener dispenser assembly being mountable to a toilet and releasing a chemical fragrance when the toilet is employed by a user, said assembly comprising:
   a dispensing unit containing a chemical fragrance, said dispensing unit releasing a measured amount of the chemical fragrance when said dispensing unit is turned on wherein said dispensing unit is configured to enhance odors associated with an area proximate said dispensing unit;
   a pair of arms, each of said arms being coupled to and extending away from said dispensing unit, each of said arms being curved thereby facilitating each of said arms to rest on a rim of a toilet bowl wherein said dispensing unit is configured to be suspended from the toilet bowl;
   a pair of switches, each of said switches being coupled to a respective one of said arms, each of said switches being positioned beneath a seat of the toilet thereby facilitating each of said switches to be turned on when a user sits on the seat, each of said switches being turned off when the user is not sitting on the seat, each of said switches being in electrical communication with said dispensing unit, said dispensing unit being turned on when said switches are turned on wherein said dispensing unit is configured to reduce odors associated with the user employing the toilet;
   wherein said dispensing unit comprises a housing having an outer wall, said outer wall having a plurality of vents each extending into an interior of said housing wherein said plurality of vents is configured to pass air therethrough;

wherein said dispensing unit includes a control circuit being positioned in said housing, said control unit receiving a first input, said control unit receiving a second input;

wherein said dispensing unit includes a pair of reservoirs, each of said reservoirs being positioned within said housing, each of said reservoirs having an outlet, each of said reservoirs containing an aerosol fragrance;

wherein said dispensing unit includes a pair of valves, each of said valves having an input and an output, each of said valves being actuatable into a closed condition to inhibit fluid communication between said input and said output, each of said valves being actuatable into an open condition to facilitate fluid communication between said input and said output;

wherein each of said valves is actuated into said open condition for a pre-determined duration of time when said control circuit receives said first input wherein each of said valves is configured to release a metered amount of the aerosol fragrance, each of said valves being actuated into said open condition two times each time said control circuit receives said first input, and wherein said dispensing unit includes a manifold being positioned within said housing, said manifold having a pair of intakes and a plurality of exhausts, each of said intakes being fluidly coupled to said output of a respective one of said valves wherein said manifold is configured to receive the aerosol fragrance, each of said exhausts being aligned with a respective one of said vents in said outer wall of said housing wherein said manifold is configured to release the aerosol fragrance through said vents.

2. The assembly according to claim 1, wherein said input of each of said valves is fluidly coupled to said outlet of a respective one of said reservoirs, each of said valves being electrically coupled to said control circuit, each of said valves being normally actuated into said closed condition wherein each of said valves is configured to retain the aerosol fragrance in said respective reservoir.

3. The assembly according to claim 1, wherein each of said valves is actuated into said open condition for a pre-determined duration of time when said control circuit receives said second input wherein each of said valves is configured to release a metered amount of the aerosol fragrance.

4. The assembly according to claim 1, wherein each of said arms extends upwardly from a top side of said outer wall of said housing, each of said arms having a distal end with respect to said housing and a top surface, each of said arms curving downwardly between said top side of said outer wall and said distal end.

5. The assembly according to claim 1, further comprising a power supply being positioned in said housing, said power supply being electrically coupled to said control circuit, said power supply comprising at least one battery.

6. An air freshener dispenser assembly being mountable to a toilet and releasing a chemical fragrance when the toilet is employed by a user, said assembly comprising:

a dispensing unit containing a chemical fragrance, said dispensing unit releasing a measured amount of the chemical fragrance when said dispensing unit is turned on wherein said dispensing unit is configured to enhance odors associated with an area proximate said dispensing unit, said dispensing unit comprising:

a housing having an outer wall, said outer wall having a plurality of vents each extending into an interior of said housing wherein said plurality of vents is configured to pass air therethrough;

a control circuit being positioned in said housing, said control circuit receiving a first input, said control circuit receiving a second input;

a pair of reservoirs, each of said reservoirs being positioned within said housing, each of said reservoirs having an outlet, each of said reservoirs containing an aerosol fragrance;

a pair of valves, each of said valves having an input and an output, each of said valves being actuatable into a closed condition to inhibit fluid communication between said input and said output, each of said valves being actuatable into an open condition to facilitate fluid communication between said input and said output, said input of each of said valves being fluidly coupled to said outlet of a respective one of said reservoirs, each of said valves being electrically coupled to said control circuit, each of said valves being normally actuated into said closed condition wherein each of said valves is configured to retain the aerosol fragrance in said respective reservoir, each of said valves being actuated into said open condition for a pre-determined duration of time when said control circuit receives said first input wherein each of said valves is configured to release a metered amount of the aerosol fragrance, each of said valves being actuated into said open condition two times each time said control circuit receives said first input, each of said valves being actuated into said open condition for a pre-determined duration of time when said control circuit receives said second input wherein each of said valves is configured to release a metered amount of the aerosol fragrance; and a manifold being positioned within said housing, said manifold having a pair of intakes and a plurality of exhausts, each of said intakes being fluidly coupled to said output of a respective one of said valves wherein said manifold is configured to receive the aerosol fragrance, each of said exhausts being aligned with a respective one of said vents in said outer wall of said housing wherein said manifold is configured to release the aerosol fragrance through said vents;

a pair of arms, each of said arms being coupled to and extending away from said dispensing unit, each of said arms being curved thereby facilitating each of said arms to rest on a rim of a toilet bowl wherein said dispensing unit is configured to be suspended from the toilet bowl, each of said arms extending upwardly from a top side of said outer wall of said housing, each of said arms having a distal end with respect to said housing and a top surface, each of said arms curving downwardly between said top side of said outer wall and said distal end;

a pair of switches, each of said switches being coupled to a respective one of said arms, each of said switches being positioned beneath a seat of the toilet thereby facilitating each of said switches to be turned on when a user sits on the seat, each of said switches being turned off when the user is not sitting on the seat, each of said switches being in electrical communication with said dispensing unit, said dispensing unit being turned on when said switches are turned on wherein said dispensing unit is configured to reduce odors associated with the user employing the toilet, each of said switches being positioned on said top surface of said respective arm, each of said switches being aligned with an apex of the curvature of said respective arm, each of said switches being electrically coupled to said control circuit, said control circuit receiving said first input when said switches are turned on, said control circuit receiving said second input when said switches are turned off after being turned on; and a power supply being positioned in said housing, said power supply being electrically coupled to said control circuit, said power supply comprising at least one battery.

\* \* \* \* \*